(12) United States Patent
Govari

(10) Patent No.: US 7,945,309 B2
(45) Date of Patent: May 17, 2011

(54) DYNAMIC METAL IMMUNITY

(75) Inventor: Assaf Govari, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 2745 days.

(21) Appl. No.: 10/302,112

(22) Filed: Nov. 22, 2002

(65) Prior Publication Data
US 2004/0102696 A1 May 27, 2004

(51) Int. Cl.
*A61B 5/05* (2006.01)
(52) U.S. Cl. .................................. 600/424; 606/130
(58) Field of Classification Search .......... 600/407–426; 606/130; 128/897–899
See application file for complete search history.

(56) References Cited

U.S. PATENT DOCUMENTS

| | | |
|---|---|---|
| 3,644,825 A | 2/1972 | Davis, Jr. et al. ............... 324/41 |
| 3,868,565 A | 2/1975 | Kuipers ........................ 324/34 R |
| 4,017,858 A | 4/1977 | Kuipers ...................... 343/100 R |
| 4,054,881 A | 10/1977 | Raab ........................ 343/112 R |
| 4,173,228 A | 11/1979 | Van Steenwyk et al. |
| 4,287,809 A | 9/1981 | Egli et al. ............................ 89/41 |
| 4,317,078 A | 2/1982 | Weed et al. .................... 324/208 |
| 4,416,289 A | 11/1983 | Bresler ........................... 128/737 |
| 4,526,177 A | 7/1985 | Rudy et al. .................... 128/737 |
| 4,560,930 A | 12/1985 | Kouno ........................... 324/207 |
| 4,605,897 A | 8/1986 | Gelinas |
| 4,613,866 A | 9/1986 | Blood .......................... 343/448 |
| 4,642,786 A | 2/1987 | Hansen ......................... 364/559 |
| 4,651,436 A | 3/1987 | Gaal .............................. 33/533 |
| 4,710,708 A | 12/1987 | Rorden et al. ................. 324/207 |
| 4,771,237 A | 9/1988 | Daley |
| 4,791,412 A | 12/1988 | Brooks |
| 4,849,692 A | 7/1989 | Blood |
| 4,905,698 A | 3/1990 | Strohl, Jr. et al. |
| 4,945,305 A | 7/1990 | Blood |
| 5,002,137 A | 3/1991 | Dickinson et al. .............. 175/19 |
| 5,042,486 A | 8/1991 | Pfeiler et al. ............. 128/653 R |
| 5,068,608 A | 11/1991 | Clark, Jr. ....................... 324/220 |
| 5,099,845 A | 3/1992 | Besz et al. |
| 5,172,056 A | 12/1992 | Voisin ...................... 324/207.17 |
| 5,211,165 A | 5/1993 | Dumoulin et al. .......... 128/653.1 |
| 5,251,635 A | 10/1993 | Dumoulin et al. .......... 128/653.1 |
| 5,253,647 A | 10/1993 | Takahashi et al. .......... 128/653.1 |
| 5,255,680 A | 10/1993 | Darrow et al. .............. 128/653.1 |

(Continued)

FOREIGN PATENT DOCUMENTS

EP 0 894 473 A 2/1999

(Continued)

OTHER PUBLICATIONS

European Search Report EP03257360 dated Mar. 12, 2004.

(Continued)

*Primary Examiner* — Long V Le
*Assistant Examiner* — Sanjay Cattungal
(74) *Attorney, Agent, or Firm* — Louis J. Capezzuto

(57) ABSTRACT

The disclosure concerns position-sensing apparatus, having radiators which generate electromagnetic energy fields and a position sensor which generates sensor signals responsive to the energy fields. Reference elements are placed at respective positions near the sensor to generate reference signals responsive to the energy fields. And, a control unit is used to calculate a position of the sensor based on sensor signals and reference element errors in order to account for the effects of interfering metal objects.

30 Claims, 2 Drawing Sheets

U.S. PATENT DOCUMENTS

| | | | |
|---|---|---|---|
| 5,265,610 A | 11/1993 | Darrow et al. | 128/653.1 |
| 5,269,289 A | 12/1993 | Takehana et al. | 128/4 |
| 5,273,025 A | 12/1993 | Sakiyama et al. | 128/6 |
| 5,274,328 A | 12/1993 | Begin et al. | |
| 5,309,913 A | 5/1994 | Kormos et al. | 128/653.1 |
| 5,325,873 A | 7/1994 | Hirschi et al. | |
| 5,375,596 A | 12/1994 | Twiss et al. | 128/653.1 |
| 5,377,678 A | 1/1995 | Dumoulin et al. | 128/653.1 |
| 5,391,199 A | 2/1995 | Ben-Haim | 607/122 |
| 5,425,367 A | 6/1995 | Shapiro et al. | |
| 5,425,382 A | 6/1995 | Golden et al. | 128/899 |
| 5,429,132 A | 7/1995 | Guy et al. | 128/653.1 |
| 5,437,277 A | 8/1995 | Dumoulin et al. | 128/653.1 |
| 5,443,489 A | 8/1995 | Ben-Haim | |
| 5,453,687 A | 9/1995 | Zierdt et al. | 324/207.17 |
| 5,553,611 A | 9/1996 | Budd et al. | |
| 5,558,091 A | 9/1996 | Acker et al. | |
| 5,577,502 A | 11/1996 | Darrow et al. | 128/653.1 |
| 5,622,169 A | 4/1997 | Golden et al. | 128/653.1 |
| 5,629,621 A | 5/1997 | Goldfine et al. | |
| 5,644,229 A | 7/1997 | Dossel et al. | |
| 5,646,524 A | 7/1997 | Gilboa | 324/207.17 |
| 5,682,886 A | 11/1997 | Delp et al. | 128/653.1 |
| 5,694,945 A | 12/1997 | Ben-Haim | 128/736 |
| 5,715,822 A | 2/1998 | Watkins et al. | 128/653.5 |
| 5,729,129 A * | 3/1998 | Acker | 324/207.12 |
| 5,752,513 A | 5/1998 | Acker et al. | 128/653.1 |
| 5,767,669 A * | 6/1998 | Hansen et al. | 324/207.12 |
| 5,769,843 A | 6/1998 | Abela et al. | 606/10 |
| 5,797,849 A | 8/1998 | Vesely et al. | 600/461 |
| 5,831,260 A | 11/1998 | Hansen | |
| 5,847,976 A | 12/1998 | Lescourret | |
| 5,879,297 A * | 3/1999 | Haynor et al. | 600/407 |
| 5,899,860 A | 5/1999 | Pfeiffer et al. | |
| 5,913,820 A | 6/1999 | Bladen et al. | |
| 5,967,980 A | 10/1999 | Ferre et al. | 600/424 |
| 5,997,473 A | 12/1999 | Taniguchi et al. | 600/117 |
| 6,073,043 A * | 6/2000 | Schneider | 600/424 |
| 6,122,538 A | 9/2000 | Sliwa, Jr. et al. | |
| 6,172,499 B1 * | 1/2001 | Ashe | 324/207.12 |
| 6,201,987 B1 | 3/2001 | Dumoulin | |
| 6,226,547 B1 | 5/2001 | Lockhart et al. | |
| 6,239,724 B1 | 5/2001 | Doron et al. | |
| 6,246,231 B1 | 6/2001 | Ashe | |
| 6,246,898 B1 * | 6/2001 | Vesely et al. | 600/424 |
| 6,366,799 B1 * | 4/2002 | Acker et al. | 600/424 |
| 6,369,564 B1 | 4/2002 | Khalfin et al. | |
| 6,373,240 B1 | 4/2002 | Govari | |
| 6,400,139 B1 * | 6/2002 | Khalfin et al. | 324/207.17 |
| 6,427,079 B1 | 7/2002 | Schneider et al. | |
| 6,493,573 B1 | 12/2002 | Martinelli et al. | |
| 6,690,963 B2 * | 2/2004 | Ben-Haim et al. | 600/424 |
| 6,774,624 B2 * | 8/2004 | Anderson et al. | 324/207.17 |
| 6,788,967 B2 * | 9/2004 | Ben-Haim et al. | 600/424 |
| 2002/0065455 A1 * | 5/2002 | Ben-Haim et al. | 600/407 |
| 2002/0165448 A1 * | 11/2002 | Ben-Haim et al. | 600/424 |

FOREIGN PATENT DOCUMENTS

| | | |
|---|---|---|
| EP | 1 174 082 A | 1/2002 |
| EP | 203 560 A | 5/2002 |
| JP | 4008341 | 1/1992 |
| JP | 10094609 | 4/1998 |
| WO | WO 92/03090 | 3/1992 |
| WO | WO 94/04938 | 3/1994 |
| WO | WO 94/23647 | 10/1994 |
| WO | WO 96/05768 A1 | 2/1996 |
| WO | WO 96/41119 | 12/1996 |
| WO | WO 97/00043 | 1/1997 |
| WO | WO 97/29678 | 8/1997 |
| WO | WO 97/29679 | 8/1997 |
| WO | WO 97/29709 | 8/1997 |
| WO | WO 97/29710 | 8/1997 |
| WO | WO 97/32179 | 9/1997 |
| WO | WO 97/42517 | 11/1997 |
| WO | WO 98/36236 | 8/1998 |
| WO | WO 99/32033 | 7/1999 |
| WO | WO 99/52430 | 10/1999 |
| WO | WO 01/34049 | 5/2001 |

OTHER PUBLICATIONS

European Search Report dated Oct. 10, 2001.
John David Jackson, "Classical Electrodynamics", Second Edition, John Wiley & Sons, New York, 1975, p. 178.
William H. Press et al., "Numerical Recipes in C, The Art of Scientific Computing", Second Edition, Cambridge University Press, ISBN 052143108, pp. 383-393.
U.S. Appl. No. 09/821,322, filed Jul. 20, 2000.*

* cited by examiner

DYNAMIC METAL IMMUNITY

FIELD OF THE INVENTION

The present invention relates generally to non-contact tracking of objects using a magnetic field, and specifically to counteracting the effect of a moving, field-responsive metal article in a magnetic field.

BACKGROUND OF THE INVENTION

Non-contact electromagnetic locating and tracking systems are well known in the art, with an exceptionally broad spectrum of applications, including such diverse topics as military target sighting, computer animation, and precise medical procedures. For example, electromagnetic locating technology is widely used in the medical field during surgical, diagnostic, therapeutic and prophylactic procedures that entail insertion and movement of objects such as surgical devices, probes, and catheters within the body of the patient. The need exists for providing real-time information for accurately determining the location and orientation of objects within the patient's body, preferably without using X-ray imaging.

U.S. Pat. Nos. 5,391,199 and 5,443,489 to Ben-Haim, which are assigned to the assignee of the present patent application and whose disclosures are incorporated herein by reference, describe systems wherein the coordinates of an intrabody probe are determined using one or more field sensors, such as Hall effect devices, coils, or other antennae carried on the probe. Such systems are used for generating three-dimensional location information regarding a medical probe or catheter. A sensor coil is placed in the catheter and generates signals in response to externally-applied magnetic fields. The magnetic fields are generated by a plurality of radiator coils, fixed to an external reference frame in known, mutually-spaced locations. The amplitudes of the signals generated in response to each of the radiator coil fields are detected and used to compute the location of the sensor coil. Each radiator coil is preferably driven by driver circuitry to generate a field at a known frequency, distinct from that of other radiator coils, so that the signals generated by the sensor coil may be separated by frequency into components corresponding to the different radiator coils.

PCT Patent Publication WO 96/05768 to Ben-Haim et al., which is assigned to the assignee of the present patent application and whose disclosure is incorporated herein by reference, describes a system that generates six-dimensional position and orientation information regarding the tip of a catheter. This system uses a plurality of sensor coils adjacent to a locatable site in the catheter, for example near its distal end, and a plurality of radiator coils fixed in an external reference frame. These coils generate signals in response to magnetic fields generated by the radiator coils, which signals allow for the computation of six location and orientation coordinates, so that the position and orientation of the catheter are known without the need for imaging the catheter.

U.S. Pat. No. 6,239,724 to Doron et al., whose disclosure is incorporated herein by reference, describes a telemetry system for providing spatial positioning information from within a patient's body. The system includes an implantable telemetry unit having (a) a first transducer, for converting a power signal received from outside the body into electrical power for powering the telemetry unit; (b) a second transducer, for receiving a positioning field signal that is received from outside the body; and (c) a third transducer, for transmitting a locating signal to a site outside the body, in response to the positioning field signal.

U.S. Pat. No. 4,173,228 to Van Steenwyk et al., whose disclosure is incorporated herein by reference, describes a catheter locating device based upon inducing a signal in a coil attached to the catheter and monitoring the amplitude and phase of the induced signal.

U.S. Pat. No. 5,099,845 to Besz et al. and U.S. Pat. No. 5,325,873 to Hirschi et al., whose disclosures are incorporated herein by reference, describe apparatus and methods in which a radiating element is fixed to a catheter, and the position of the catheter is determined responsive to energy radiated from the element.

U.S. Pat. No. 5,425,382 to Golden, et al., whose disclosure is incorporated herein by reference, describes apparatus and methods for locating a catheter in the body of a patient by sensing the static magnetic field strength gradient generated by a magnet fixed to the catheter.

U.S. Pat. No. 4,905,698 to Strohl, Jr. et al. and U.S. Pat. No. 5,425,367 to Shapiro et al., whose disclosures are incorporated herein by reference, describe apparatus and methods wherein an applied magnetic field induces currents within a coil at the tip of a catheter. Based on these currents, the relative location of the catheter is determined.

U.S. Pat. No. 5,558,091 to Acker et al., which is assigned to the assignee of the present patent application and whose disclosure is incorporated herein by reference, describes a magnetic position and orientation determining system which uses uniform fields from Helmholtz coils positioned on opposite sides of a sensing volume and gradient fields generated by the same coils. By monitoring field components detected at a probe during application of these fields, the position and orientation of the probe is deduced. A representation of the probe is superposed on a separately-acquired image of the subject to show the position and orientation of the probe with respect to the subject.

U.S. Pat. No. 5,913,820 to Bladen et al., whose disclosure is incorporated herein by reference, describes apparatus for locating the position of a sensor, preferably in three dimensions, by generating magnetic fields that are detected at the sensor. The magnetic fields are generated from a plurality of locations and enable both the orientation and location of a single coil sensor to be determined.

Commercial electrophysiological and physical mapping systems based on detecting the position of a probe inside the body are presently available. Among them, CARTO™, developed and marketed by Biosense Webster, Inc. (Diamond Bar, Calif.), is a system for automatic association and mapping of local electrical activity with catheter location.

Electromagnetic locating and tracking systems are susceptible to inaccuracies when a metal or other magnetically-responsive article is introduced into the vicinity of the object being tracked. Such inaccuracies occur because the magnetic fields generated in this vicinity by the location system's radiator coils are distorted. For example, the radiator coils' magnetic fields may generate eddy currents in such an article, and the eddy currents then cause parasitic magnetic fields that react with the field that gave rise to them. In a surgical environment, for example, there is a substantial amount of conductive and permeable material including basic and ancillary equipment (operating tables, carts, movable lamps, etc.) as well as invasive surgery apparatus (scalpels, catheters, scissors, etc.). The eddy currents generated in these articles and the resultant electromagnetic field distortions can lead to errors in determining the position of the object being tracked.

It is known to address the problem of the interference of static metal objects by performing an initial calibration, in which the response of the system to a probe placed at a relatively large number of points of interest is measured. This may be acceptable for addressing stationary sources of electromagnetic interference, but it is not satisfactory for solving the interference problems induced by moving metallic and conductive objects.

U.S. Pat. No. 6,373,240 to Govari, entitled, "Counteracting Metal Presence In A Magnetic Tracking System," which is assigned to the assignee of the present patent application and is incorporated herein by reference, describes an object tracking system comprising one or more sensor coils adjacent to a locatable point on an object being tracked, and one or more radiator coils, which generate alternating energy fields comprising magnetic fields, in a vicinity of the object when driven by respective alternating electrical currents. For each radiator coil, a frequency of its alternating electrical current is scanned through a plurality of values so that, at any specific time, each of the radiator coils radiates at a frequency which is different from the frequencies with which the other radiator coils are radiating.

The sensor coils generate electrical signals responsive to the magnetic fields, which signals are received by signal processing circuitry and analyzed by a computer or other processor. When a metal or other field-responsive article is in the vicinity of the object, the signals typically include position signal components responsive to the magnetic fields generated by the radiator coils at their respective instantaneous driving frequencies, and parasitic signal components responsive to parasitic magnetic fields generated because of the article. The parasitic components are typically equal in frequency to the instantaneous frequency of the driving frequency, but are shifted in phase, so that the effect at each sensor coil is to produce a combined signal having a phase and an amplitude which are shifted relative to the signal when no field-responsive article is present. The phase-shift is a function of the driving frequency, and so will vary as each driving frequency is scanned. The computer processes the combined signal to find which frequency produces a minimum phase-shift, and thus a minimum effect of the parasitic components, and this frequency is used to calculate the position of the object. Varying the driving frequency until the phase shift is a minimum is described as an effective method for reducing the effect of field-responsive articles on the signal.

U.S. Pat. No. 6,172,499 to Ashe, whose disclosure is incorporated herein by reference, describes a device for measuring the location and orientation in the six degrees of freedom of a receiving antenna with respect to a transmitting antenna utilizing multiple-frequency AC magnetic signals. The transmitting component consists of two or more transmitting antennae of known location and orientation relative to one another. The transmitting antennae are driven simultaneously by AC excitation, with each antenna occupying one or more unique positions in the frequency spectrum. The receiving antennae measure the transmitted AC magnetic field plus distortions caused by conductive metals. A computer then extracts the distortion component and removes it from the received signals, providing the correct position and orientation output.

U.S. Pat. No. 6,246,231 to Ashe, whose disclosure is incorporated herein by reference, describes a method of flux containment in which the magnetic fields from transmitting elements are confined and redirected from the areas where conducting objects are commonly found.

U.S. Pat. No. 5,767,669 to Hansen et al., whose disclosure is incorporated herein by reference, describes a method for subtracting eddy current distortions produced in a magnetic tracking system. The system utilizes pulsed magnetic fields from a plurality of generators, and the presence of eddy currents is detected by measuring rates of change of currents generated in sensor coils used for tracking. The eddy currents are compensated for by adjusting the duration of the magnetic pulses.

U.S. Pat. Nos. 4,945,305 and 4,849,692 to Blood, whose disclosures are incorporated herein by reference, describe tracking systems that circumvent the problems of eddy currents by using pulsed DC magnetic fields. Sensors which are able to detect DC fields are used in the systems, and eddy currents are detected and adjusted for by utilizing the decay characteristics and the amplitudes of the eddy currents.

U.S. Pat. No. 4,791,412 to Brooks, whose disclosure is incorporated herein by reference, describes an article surveillance system utilizing encoded magnetic markers and incorporating a signal processing technique for reducing the effects of large metal objects in the surveillance zone.

U.S. Pat. No. 6,400,139 to Khalfin et al., whose disclosure is incorporated herein by reference, describes a probe tracking system designed to operate in an environment characterized by electromagnetic distortion, such as that caused by eddy currents. The system employs at least one stationary sensor (a "witness sensor") having a fixed position and orientation near or within a volume of interest. One or more probe sensors are placed on an object to be tracked within the volume, and the output of each witness sensor is used to compute the parameters of a non-real effective electromagnetic source. The parameters of the effective source are used as inputs to the computation of position and orientation as measured by each probe sensor, as if the object were in the non-distorted electromagnetic field produced by the effective source or sources.

U.S. Pat. No. 6,369,564 to Khalfin et al., whose disclosure is incorporated herein by reference, describes a probe tracking system designed to operate in an environment characterized by strong electromagnetic distortion. The system includes at least one source of an AC electromagnetic field, at least one witness sensor measuring components of the electromagnetic induction vector at known locations near or within the volume of interest, and at least one wireless probe sensor placed on the object being tracked. The wireless sensor has a known response or distortion to the electromagnetic field generated by the primary source. Data from the witness sensors are used to locate the probe sensor, treating the probe sensor as a secondary source of the AC electromagnetic field, that is, as a transponder with initially known magnetic parameters. This information is utilized to define coordinates and attitude of the secondary source and, in turn, the position and orientation of the object of interest. Preferably, the probe sensor is an LC-contour tuned to the frequency of the tracker source.

U.S. Pat. No. 6,226,547 to Lockhart et al., whose disclosure is incorporated herein by reference, describes a catheter tracking system that includes a plurality of magnetic field transducers, at least one of which is disposed on the catheter, and others of which are located in/or around the body of the patient and which serve as reference transducers. Magnetic field signals are used to determine the position of the catheter with respect to the reference transducers.

U.S. Pat. No. 5,847,976 to Lescourret, whose disclosure is incorporated herein by reference, describes a method using electromagnetic fields for tracking a mobile system that is placed in a carrier and linked to a magnetic field sensor. The method includes modeling the electromagnetic fields as a function of the coordinates of the sensor, a first field being created by the transmitter, a second field being created by the electrical currents induced in the carrier by the first field, and a third field being created by the electrical currents induced in the mobile system by the first two fields, the magnetic effect of each field being characterized independently of the effects of the other fields by the coefficients of a model thereof. The method further includes real-time computation of the position and orientation of the sensor by using a current measurement of the electromagnetic field at the sensor and by using the models of the fields, the position and orientation of the sensor being defined from a measured field from which the third field is deduced.

U.S. Pat. No. 6,427,079 to Schneider et al., whose disclosure is incorporated herein by reference, describes a remote location determination system that uses splines of magnetic field values to determine location parameters. An automatic calibration technique is described as compensating for any variations in gain in a sensor and related components. Methods for reducing the effects of eddy currents in surrounding conductive objects are described.

U.S. Pat. No. 6,201,987 to Dumoulin, whose disclosure is incorporated herein by reference, describes a tracking system that modifies current patterns applied to its transmit coils in order to compensate for the effect of the eddy currents. The current supplied to the coils is a linear combination of the current needed to create the desired electromagnetic field in the region of interest, and one or more error terms. These terms are determined experimentally during system calibration and are mathematically modeled as a series of exponential functions having a given amplitude and time constant. The error terms in the current applied to the transmit coils are described as canceling the magnetic fields created by eddy currents within the tracking region and as resulting in an actual electromagnetic field which is close to the desired ideal electromagnetic field. The fidelity of the electromagnetic field is described as being further increased by reducing eddy currents within the eddy current inducing structures. This is done by constructing shield coils which are placed between the transmit coil and the eddy current inducing structures. These shield coils are described as creating canceling magnetic fields within the eddy current-inducing structures without substantially altering the electromagnetic fields in the region over which the invasive device is tracked.

U.S. Pat. No. 5,831,260 to Hansen, whose disclosure is incorporated herein by reference, describes a combined electromagnetic and optical hybrid locating system that is intended to reduce the disadvantages of each individual system operating alone.

U.S. Pat. No. 6,122,538 to Sliwa, Jr. et al., whose disclosure is incorporated herein by reference, describes hybrid position and orientation systems using different types of sensors including ultrasound, magnetic, tilt, gyroscopic, and accelerometer subsystems for tracking medical imaging devices.

In the prior art, there is no straightforward, accurate, real-time method that addresses the problem of interference induced in electromagnetic locating and tracking systems caused by the introduction of non-stationary metallic or other magnetically-responsive articles into the measurement environment.

SUMMARY OF THE INVENTION

It is an object of some aspects of the present invention to provide apparatus and methods for improving the accuracy of electromagnetic locating and tracking systems.

It is a further object of some aspects of the present invention to provide apparatus and methods for utilizing electromagnetic locating and tracking systems without the need for prolonged initial calibration procedures.

It is yet a further aspect of some aspects of the present invention to provide apparatus and methods for increasing accuracy of electromagnetic location and tracking systems without concern for the presence of moving metallic and conductive materials in the space wherein measurements are being taken.

It is still a further object of some aspects of the present invention to provide apparatus and methods for enabling electromagnetic location and tracking systems to function accurately in the presence of moving metallic and conductive materials in the space wherein the measurements are being taken, without regard to the quantity of such materials, their conductive characteristics, velocities, orientation, direction and the length of time that such materials are within the space.

It is an additional object of some aspects of the present invention to provide apparatus and methods for operating electromagnetic location and tracking systems without the necessity of employing means for reducing or circumventing the effects caused by eddy currents induced in moving conductive objects in the space wherein measurements are being taken.

It is still an additional object of some aspects of the present invention to provide apparatus and methods for utilizing the eddy currents produced in moving objects comprising conductive materials in the space wherein measurements are being taken to improve the accuracy of electromagnetic location and tracking systems.

In preferred embodiments of the present invention, apparatus for electromagnetic locating and tracking comprises a probe whose position is tracked in a space, a plurality of electromagnetic radiators located in the vicinity of the space, a plurality of fixed reference elements whose positions are known, and a control unit adapted to drive the radiators and process signals from the probe and reference elements. When a metal or magnetic field-responsive object, for example a surgical tool, movable lamp, cart, etc., is introduced into the vicinity of the probe and reference elements, the magnetic field values generated by field sensors of the probe and the reference elements differ from the undistorted magnetic field values that would have been generated in the absence of the interfering object. To compensate for this interference effect, corrected magnetic field values are calculated for the field sensors of the probe by using an interpolation algorithm whose inputs include the measured magnetic field values of the field sensors of the probe, the measured magnetic field values of each reference element, and, for each reference element, the errors in magnetic field values caused by the presence of the interfering object. These corrected magnetic field values are then used to determine the absolute position of the probe.

Advantageously, these embodiments of the present invention do not generally require extensive initial calibration, nor is it typically necessary to employ cumbersome means to reduce or circumvent the effects caused by eddy currents induced in non-stationary conductive objects in the space.

Further advantageously, these embodiments of the present invention typically achieve the objective of accurate tracking regardless of the number of metal objects introduced to the surrounding space, their conductive characteristics, velocities, orientations, directions and the lengths of time that the objects are within the space.

In some preferred embodiments of the present invention, an uncorrected position of the probe is determined using uncorrected, distorted magnetic field values generated by the field sensors of the probe in the presence of an interfering object. This uncorrected position is then corrected using a spatial interpolation algorithm. To compensate for the effect of the interfering object on the probe, the absolute position of the probe is calculated with a high degree of accuracy by using a spatial interpolation algorithm whose inputs include the determined uncorrected position of the probe and determined position offsets of the reference elements caused by the interfering object. To illustrate the calculation performed in these preferred embodiments to determine the absolute position of the probe, a simple example is shown in the following table in which the probe is located between two reference elements.

|  | Measurements of Position (cm) | | |
| --- | --- | --- | --- |
|  | Absolute | Distorted | Calculated |
| Reference element #1 | 0.0 | 0.1 | 0.0 |
| Probe | — | 0.5 | 0.4 |
| Reference element #2 | 10.0 | 10.0 | 10.0 |

In this example, the absolute positions of the reference elements are known prior to a procedure. During the procedure, after the introduction of a conductive object into the vicinity of the probe and of the reference elements, the determined position of reference element #1 shifts 0.1 cm from its known absolute position towards reference element #2. To determine the absolute position of the probe, its uncorrected position is shifted in the opposite direction (away from reference element #2) by a distance approximately equal to the 0.1 cm shift experienced by reference element #1, resulting in a calculated position of 0.4 cm. For purposes of this simplified example, it is assumed that the conductive object has approximately the same offsetting effect on the probe as it does on reference element #1 because of their close mutual proximity. In actual practice, the shifts would differ and would be calculated by interpolation, as described hereinbelow.

In some preferred embodiments of the present invention, the control unit is coupled by leads to the probe, reference elements and radiators. Alternatively, the probe and/or reference elements comprise circuitry which transmits wireless signals responsive to electromagnetic radiation generated by the radiators.

For some applications, apparatus and methods described herein are adapted to work in conjunction with apparatus and methods described in co-pending U.S. patent application Ser. No. 09/621,322, entitled, "Medical System Calibration With Static Metal Compensation," filed Jul. 20, 2000, which is assigned to the assignee of the present patent application and is incorporated herein by reference.

There is therefore provided, in accordance with a preferred embodiment of the present invention, position-sensing apparatus, including:

a set of radiators, which are adapted to be placed at respective positions in a vicinity of a body of a subject and to generate electromagnetic energy fields;

a position sensor, which is adapted to placed in the body of the subject and to generate sensor signals responsive to the energy fields;

one or more reference elements, which are adapted to be placed at respective positions in a vicinity of the sensor and to generate reference signals responsive to the energy fields; and a control unit, which is adapted to:

determine, for each of the reference elements, respective undistorted reference parameters, responsive to the positions of the reference elements, receive the sensor signals and the reference signals, calculate a reference element error for each reference element, responsive to an interaction of a metal article with the energy fields, responsive to the undistorted reference parameter of the reference element, and responsive to the reference signal generated by the reference element, and calculate a position of the sensor, responsive to the sensor signals and the reference element errors.

Preferably, at least one of the one or more reference elements is adapted to be placed outside of the body of the subject. Additionally, at least one of the one or more reference elements is typically adapted to be placed at a fixed, known position relative to the set of radiators during operation of the apparatus.

In some preferred embodiments, the control unit is adapted to calculate corrected sensor signals responsive to the reference element errors and responsive to the generated sensor signals, and to calculate the position of the sensor responsive to the corrected sensor signals. Preferably, the control unit is adapted to designate the reference element error, for at least one of the reference elements, to be responsive to a measured magnetic field value at the at least one of the reference elements, which value is responsive to the interaction of the metal article with the energy fields.

In a preferred embodiment, the control unit is adapted to calculate the undistorted reference parameter of at least one of the reference elements responsive to a relative position of the at least one of the reference elements with respect to the set of radiators. In this case, the control unit is preferably adapted to perform the calculation of the reference parameter substantially independently of the interaction of the metal article with the energy fields. Further preferably, the control unit is adapted to calculate the undistorted reference parameter of the at least one of the reference elements responsive to a calculation of a magnetic field value at the at least one of the reference elements, which value is responsive to the relative position of the at least one of the reference elements with respect to the set of radiators.

In a preferred embodiment, the control unit is adapted to determine the undistorted reference parameter of at least one of the reference elements responsive to a measurement that is responsive to a relative position of the at least one of the reference elements with respect to the set of radiators. Typically, the control unit is adapted to determine the undistorted reference parameter of the at least one of the reference elements substantially independently of the interaction of the metal article with the energy fields. The control unit is preferably adapted to determine the undistorted reference parameter of the at least one of the reference elements responsive to a measurement of a magnetic field value at the at least one of the reference elements.

For some applications, for at least one of the one or more reference elements, the control unit is adapted to substantially equate the undistorted reference parameter with the position of the reference element. For example, the control unit may be adapted to designate the reference element error, for the at least one of the one or more reference elements, to be an apparent spatial offset of the reference element responsive to the interaction of the metal article with the energy fields.

In a preferred embodiment, the one or more reference elements include at least three reference elements, adapted to be placed at three non-collinear positions in a vicinity of the sensor. For some applications, the at least three reference elements include at least four reference elements, adapted to be placed at four non-coplanar positions in a vicinity of the sensor.

There is further provided, in accordance with a preferred embodiment of the present invention, a method for sensing a position of a sensor placed within a body of a subject, including:

determining, for reference positions in a vicinity of the sensor, respective undistorted reference parameters;

generating electromagnetic energy fields at field-generating positions in a vicinity of the body of the subject;

generating reference signals at the reference positions, responsive to the energy fields and responsive to an interaction of a metal article with the energy fields;

calculating a reference error corresponding to each reference position, responsive to the undistorted reference parameter of the reference position and responsive to the reference signal generated at the reference position;

generating sensor signals from the sensor, responsive to the energy fields and responsive to the interaction of the metal article with the energy fields; and calculating a position of the sensor, responsive to the sensor signals and the reference errors.

The present invention will be more fully understood from the following detailed description of a preferred embodiment thereof, taken together with the drawings, in which:

DETAILED DESCRIPTION OF PREFERRED EMBODIMENTS

Figure 1:
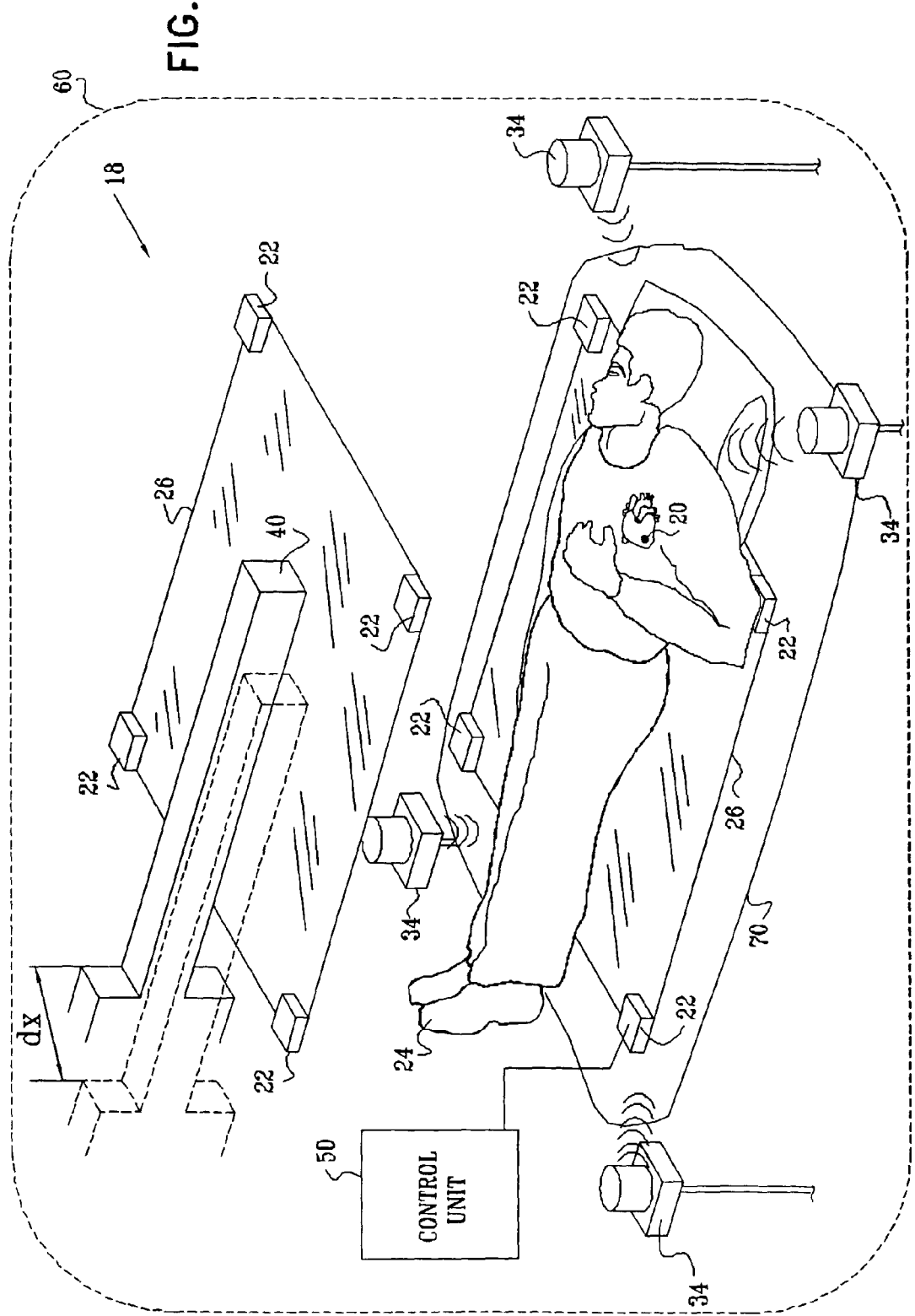
FIG. 1 is a schematic, pictorial illustration of an electromagnetic locating and tracking system used during a medical procedure, in accordance with a preferred embodiment of the present invention.

FIG. 1 is a schematic, pictorial illustration of an electromagnetic locating and tracking system 18 utilized to track a position-sensing probe 20 in the body of a patient 24 while providing immunity to the movement (dx) of a conductive object 40 in or near a space 60 around the patient 24, in accordance with a preferred embodiment of the present invention. System 18 comprises a set of radiators 34, which are driven by a control unit 50 to track probe 20, preferably but not necessarily using methods and apparatus which are described in the above-cited US Patents and PCT Patent Publication to Ben-Haim and Ben-Haim et al. Thus, probe 20 preferably comprises one or more field sensors, such as Hall effect devices, coils, or other antennae, for use in position determination. Alternatively or additionally, other methods and apparatus known in the art are used to facilitate the tracking of probe 20.

Control unit 50 comprises circuitry for processing signals received from probe 20 and from one or more reference elements 22, and for calculating the absolute position of probe 20 using an interpolation algorithm, as described hereinbelow.

Conductive object 40 typically comprises a metal or magnetic field-responsive article, for example a surgical tool, movable lamp, cart, etc. Conductive object 40 generates parasitic fields, the phases and amplitudes of which generally depend on properties of conductive object 40, including its dielectric constant, magnetic permeability, and geometrical shape. It will be appreciated that although conductive object 40 is shown in FIG. 1 as a single object, conductive object 40 could comprise a number of separate conductive objects, which are often brought in and out of the area of a medical procedure.

In a preferred embodiment of the present invention, system 18 comprises a plurality of fixed reference elements 22, preferably four or more non-coplanar elements. The absolute positions of reference elements 22 are known by, for example, attaching them to frames 26, which, in turn, are fixed to an operating table 70. Reference elements 22 preferably but not necessarily comprise location field sensors that are substantially identical to those in probe 20, so that conducting object 40 has the same potential interference effect on the measured position of probe 20 as it does on the measured position of reference elements 22. Using the known absolute positions of reference elements 22, the magnetic field values that would be measured by the field sensors of the reference elements in the absence of object 40 in space 60 (the "undistorted magnetic field values") are obtained by: (a) calculation, based on the relative positional and angular dispositions of each reference element with respect to each field generator of each radiator 34, and/or (b) measurement, in the absence of object 40, of the magnetic field at each reference element responsive to the fields generated by the radiators. These undistorted magnetic field values are preferably stored in a memory (not shown) of control unit 50. During a procedure, probe 20 preferably remains within a space generally bounded by the positions of reference elements 22, so as to typically limit calculations to interpolation based on the magnetic fields at the reference elements, rather than extrapolation.

When conductive object 40 is introduced into the vicinity of space 60, the magnetic field values generated by the field sensors of probe 20 and reference elements 22 differ from the undistorted magnetic field values that would have been generated if object 40 were not present in space 60. The error differs for each reference element 22, responsive to the location and orientation of each reference element 22 relative to conductive object 40, the particular conductive properties of conductive object 40, the shape and orientation of conductive object 40, and other factors. Corrected magnetic field values are preferably calculated for the field sensors of probe 20 by an interpolation algorithm whose inputs include the measured magnetic field values for the field sensors of probe 20, the measured magnetic field values for each reference element 22, and the determined object-induced errors in magnetic field values of each reference element 22. The algorithm preferably uses non-linear interpolation, such as geometric interpolation. These corrected magnetic field values for the field measured by the field sensors of probe 20 are then used by control unit 50 to determine the absolute location and orientation of probe 20.

Preferably, a relatively large number of reference elements 22 are placed at representative fixed locations in space 60, so as to increase the accuracy of the interpolations. Reference elements 22 are preferably positioned as close to the expected vicinity of probe 20 as is feasible, so as to increase the accuracy of interpolations.

Since conductive objects, such as tools and support equipment, are frequently moved during medical procedures, it is generally preferable to update the distorted magnetic field values generated by reference elements 22, and resulting error values, substantially each time that an updated determination of the position of probe 20 is made, or as deemed appropriate by an operator of system 18.

In another preferred embodiment of the present invention, an uncorrected position of probe 20 is determined using uncorrected magnetic field values generated by the field sensors of probe 20. This uncorrected position is corrected using a spatial interpolation algorithm, as described below. When conductive object 40 is introduced into the vicinity of space 60, the positions of probe 20 and reference elements 22, as determined using uncorrected magnetic field values generated by the field sensors of probe 20 and reference elements 22, differ from their true positions. The direction and magnitude of these offsets differ for each reference element 22, responsive to the location and orientation of each reference element 22 relative to conductive object 40, the particular conductive properties of conductive object 40, the shape and orientation of conductive object 40, and other factors. A corrected position of probe 20 is preferably calculated by using a spatial non-linear interpolation algorithm whose inputs include the determined uncorrected position of probe 20 and the object-induced offsets of reference elements 22. In particular, by analyzing the induced offsets of reference elements 22, control unit 50 preferably determines the interference effect conductive object 40 has on the point in space 60 at the measured coordinates of probe 20, and compensates for this effect.

Preferably, a relatively large number of reference elements 22 are placed at representative fixed locations in space 60 so as to increase the accuracy of the interpolations. Reference elements 22 are preferably positioned as close to the expected vicinity of probe 20 as is feasible so as to increase the accuracy of interpolations.

Figure 2:
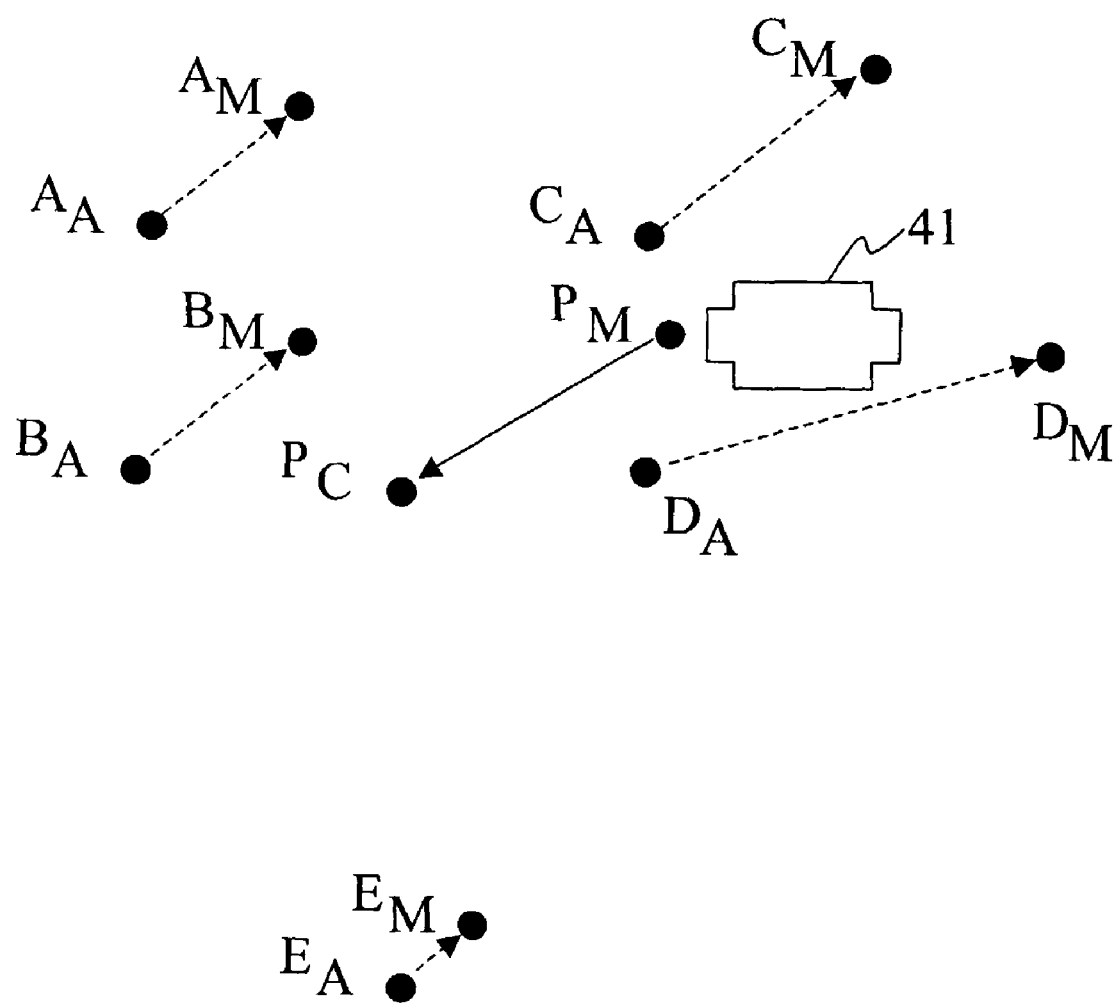
FIG. 2 is a two-dimensional schematic diagram illustrating a simplified example of determination of the absolute position of a probe, in accordance with a preferred embodiment of the present invention.

Reference is now made to FIG. 2, which is a two-dimensional schematic diagram illustrating a simplified example determination of a calculated absolute position $P_C$ of a probe, in accordance with a preferred embodiment of the present invention. Points $A_A$, $B_A$, $C_A$, $D_A$, and $E_A$, represent known absolute positions of five reference elements 22, for example A, B, C, D, and E. Points $A_M$, $B_M$, $C_M$, $D_M$, and $E_M$ represent the reference elements' 22 respective determined measured (uncorrected) positions during a procedure, after the introduction of a conductive object 41 into the vicinity of the probe and reference elements. A significant offset between the known position of one of the reference elements 22 (at positions A, B, C, D and E) and the measured position indicates that the reference element 22—and consequently the space surrounding the reference element 22—is strongly affected by the conductive object. Reference element 22 at position D is an example of such a reference element. Conversely, a small or insubstantial offset (e.g., that of reference element at position E) indicates that conductive object 41 has little effect on the space immediately surrounding the reference element.

The measured (uncorrected) position $P_M$ of the probe and the calculated offsets of reference elements at positions A, B, C, D, and E are preferably input into a spatial interpolation algorithm, which calculates the corrected absolute position $P_C$ of the probe. In this simplified example, the measured positions of the reference elements 22 are offset to varying degrees up and to the right of their known absolute positions, so the corrected position $P_C$ of the probe is preferably correspondingly offset by control unit 50 down and to the left of the measured position $P_M$ of the probe, in order to compensate for the position-distorting effect of conductive object 41. The effect of spatial interpolation is seen in the figure in that the correction applied to the probe's position is largely, but not entirely, based on the measured offsets of reference elements C and D, which are closest to the probe.

It is to be understood that preferred embodiments of the present invention are described herein with respect to invasive medical techniques by way of example only.

The scope of the present invention includes application of the techniques described herein to electromagnetic locating and tracking systems used for any purpose whatsoever.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Position-sensing apparatus, comprising:
  a set of radiators, which are adapted to be placed at respective positions in a vicinity of a body of a subject and to generate electromagnetic energy fields;
  a position sensor, which is adapted to placed in the body of the subject and to generate sensor signals responsive to the energy fields;
  one or more reference elements, which are adapted to be placed at fixed respective positions in a vicinity of the sensor and to generate reference signals responsive to the energy fields; and
  a control unit, which is adapted to:
  determine and store in memory, for each of the reference elements, respective undistorted reference parameters as undistorted magnetic field values, responsive to the positions of the reference elements,
  receive the sensor signals and the reference signals,
  calculate a reference element error for each reference element, responsive to an interaction of a metal article with the energy fields, responsive to the stored undistorted magnetic field values of the reference element, and responsive to the reference signal generated by the reference element, and
  calculate a position of the sensor, responsive to the sensor signals and the reference element errors.

2. Apparatus according to claim 1, wherein at least one of the one or more reference elements is adapted to be placed outside of the body of the subject.

3. Apparatus according to claim 1, wherein at least one of the one or more reference elements is adapted to be placed at a fixed, known position relative to the set of radiators during operation of the apparatus.

4. Apparatus according to claim 1, wherein the control unit is adapted to calculate corrected sensor signals responsive to the reference element errors and responsive to the generated sensor signals, and to calculate the position of the sensor responsive to the corrected sensor signals.

5. Apparatus according to claim 1, wherein the control unit is adapted to designate the reference element error, for at least one of the reference elements, to be responsive to a measured magnetic field value at the at least one of the reference elements, which value is responsive to the interaction of the metal article with the energy fields.

6. Apparatus according to claim 1, wherein the control unit is adapted to calculate the undistorted reference parameter of at least one of the reference elements responsive to a relative position of the at least one of the reference elements with respect to the set of radiators.

7. Apparatus according to claim 6, wherein the control unit is adapted to perform the calculation of the reference parameter substantially independently of the interaction of the metal article with the energy fields.

8. Apparatus according to claim 6, wherein the control unit is adapted to calculate the undistorted reference parameter of the at least one of the reference elements responsive to a calculation of a magnetic field value at the at least one of the reference elements, which value is responsive to the relative position of the at least one of the reference elements with respect to the set of radiators.

9. Apparatus according to claim 1, wherein the control unit is adapted to determine the undistorted reference parameter of at least one of the reference elements responsive to a measurement that is responsive to a relative position of the at least one of the reference elements with respect to the set of radiators.

10. Apparatus according to claim 9, wherein the control unit is adapted to determine the undistorted reference parameter of the at least one of the reference elements substantially independently of the interaction of the metal article with the energy fields.

11. Apparatus according to claim 9, wherein the control unit is adapted to determine the undistorted reference parameter of the at least one of the reference elements responsive to a measurement of a magnetic field value at the at least one of the reference elements.

12. Apparatus according to claim 1, wherein, for at least one of the one or more reference elements, the control unit is adapted to substantially equate the undistorted reference parameter with the position of the reference element.

13. Apparatus according to claim 12, wherein the control unit is adapted to designate the reference element error, for the at least one of the one or more reference elements, to be an apparent spatial offset of the reference element responsive to the interaction of the metal article with the energy fields.

14. Apparatus according to claim 1, wherein the one or more reference elements comprise at least three reference elements, adapted to be placed at three non-collinear positions in a vicinity of the sensor.

15. Apparatus according to claim 14, wherein the at least three reference elements comprise at least four reference elements, adapted to be placed at four non-coplanar positions in a vicinity of the sensor.

16. A method for sensing a position of a sensor placed within a body of a subject, comprising:
Determining and storing, for reference positions fixed in a vicinity of the sensor, respective undistorted reference parameters as undistorted magnetic field values;
generating electromagnetic energy fields at field-generating positions in a vicinity of the body of the subject;
generating reference signals at the reference positions, responsive to the energy fields and responsive to an interaction of a metal article with the energy fields;
calculating a reference error corresponding to each reference position, responsive to the stored undistorted magnetic field value of the reference position and responsive to the reference signal generated at the reference position;
generating sensor signals from the sensor, responsive to the energy fields and responsive to the interaction of the metal article with the energy fields; and
calculating a position of the sensor, responsive to the sensor signals and the reference errors.

17. A method according to claim 16, wherein generating the reference signals comprises generating the reference signals at reference positions outside of the body of the subject.

18. A method according to claim 16, wherein generating the reference signals comprises generating the reference signals at fixed, known positions relative to the field-generating positions.

19. A method according to claim 16, comprising calculating corrected sensor signals responsive to the reference errors and responsive to the generated sensor signals, wherein calculating the position of the sensor comprises calculating the position responsive to the corrected sensor signals.

20. A method according to claim 16, wherein calculating the reference error comprises:
measuring a magnetic field value at at least one of the reference positions, responsive to the interaction of the metal article with the energy fields; and
designating the reference error corresponding to the at least one of the reference positions to be responsive to the measured magnetic field value.

21. A method according to claim 16, wherein determining the undistorted reference parameters comprises calculating the undistorted reference parameter for at least one of the reference positions responsive to a relative position of the at least one of the reference positions with respect to the field-generating positions.

22. A method according to claim 21, wherein calculating the undistorted reference parameter comprises calculating the undistorted reference parameter substantially independently of the interaction of the metal article with the energy fields.

23. A method according to claim 21, wherein calculating the undistorted reference parameter for the at least one of the reference positions comprises calculating a magnetic field value at the at least one of the reference positions, responsive to the relative position of the at least one of the reference positions with respect to the field-generating positions.

24. A method according to claim 16, wherein determining the undistorted reference parameter for at least one of the reference positions comprises measuring a value that is responsive to a relative position of the at least one of the reference positions with respect to the field-generating positions.

25. A method according to claim 24, wherein measuring the value comprises measuring the value substantially independently of the interaction of the metal article with the energy fields.

26. A method according to claim 24, wherein measuring the value comprises measuring a magnetic field value at the at least one of the reference positions.

27. A method according to claim 16, wherein determining the undistorted reference parameter for at least one of the reference positions comprises substantially equating the undistorted reference parameter with the reference position.

28. A method according to claim 27, wherein calculating the reference error comprises designating the reference error, for the at least one of the reference positions, to be an apparent spatial offset of the reference position responsive to the interaction of the metal article with the energy fields.

29. A method according to claim 16, wherein generating the reference signals comprises generating the reference signals at at least three non-collinear reference positions.

30. A method according to claim 29, wherein generating the reference signals comprises generating the reference signals at at least four non-coplanar reference positions.

* * * * *